(12) United States Patent
Lee et al.

(10) Patent No.: US 11,306,119 B2
(45) Date of Patent: Apr. 19, 2022

(54) PEPTIDE BOUND TO PD-L1 AND USE THEREOF

(71) Applicant: KYUNGPOOK NATIONAL UNIVERSITY INDUSTRY-ACADEMIC COOPERATION FOUNDATION, Daegu (KR)

(72) Inventors: Byung-Heon Lee, Daegu (KR); Smriti Gurung, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 5 days.

(21) Appl. No.: 16/772,809

(22) PCT Filed: Dec. 17, 2018

(86) PCT No.: PCT/KR2018/016021
§ 371 (c)(1),
(2) Date: Jun. 15, 2020

(87) PCT Pub. No.: WO2019/117690
PCT Pub. Date: Jun. 20, 2019

(65) Prior Publication Data
US 2021/0163534 A1   Jun. 3, 2021

(30) Foreign Application Priority Data
Dec. 15, 2017  (KR) .................. 10-2017-0173304
Dec. 14, 2018  (KR) .................. 10-2018-0161980

(51) Int. Cl.
| C07K 7/06 | (2006.01) |
| A61P 35/00 | (2006.01) |
| A61K 38/00 | (2006.01) |
| C07K 14/705 | (2006.01) |
| G01N 33/574 | (2006.01) |

(52) U.S. Cl.
CPC ............ *C07K 7/06* (2013.01); *A61P 35/00* (2018.01); *C07K 14/70503* (2013.01); *G01N 33/574* (2013.01); *A61K 38/00* (2013.01)

(58) Field of Classification Search
CPC ............ C07K 7/06; A61P 35/00; A61K 38/00
See application file for complete search history.

(56) References Cited

U.S. PATENT DOCUMENTS

| 7,267,942 B2 * | 9/2007 | Peiris ............... C07H 21/04 435/5 |
| 9,815,897 B2 | 11/2017 | King et al. |
| 2004/0123343 A1 * | 6/2004 | La Rosa ............ C07K 14/415 800/278 |
| 2013/0330335 A1 * | 12/2013 | Bremel ............... G16B 20/00 424/134.1 |
| 2018/0155394 A1 | 6/2018 | Lee et al. |
| 2018/0201651 A1 | 7/2018 | Lee et al. |

FOREIGN PATENT DOCUMENTS

| KR | 10-1741594 B1 | 5/2017 |
| KR | 10-1750549 B1 | 7/2017 |
| KR | 10-2017-0109644 A | 9/2017 |
| WO | WO 2008/021290 | * 2/2008 ............... C12P 1/00 |
| WO | WO 2009/091518 | * 7/2009 ............... A01H 5/00 |
| WO | 2016-111645 A1 | 7/2016 |

OTHER PUBLICATIONS

Crits-Christoph et al., 2018, Novel soil bacteria possess diverse genes for secondary metabolic biosynthesis, Nature, 558: 440-444 (12 supplemental pages).*
International Search Report for PCT/KR2018/016021 dated Apr. 10, 2019 from Korean Intellectual Property Office.
Yamane, Hiromichi et al., "Programmed cell death protein 1 and programmed death-ligand 1 are expressed on the surface of some small-cell lung cancer lines", Am. J. Cancer Res., 2015, vol. 5, No. 4, pp. 1553-1557.
NCBI, GenBank accession No. XP_020324614.1 (Mar. 13, 2017).
NCBI, GenBank accession No. PID97313.1 (Nov. 3, 2017).
Database UniProt [Online] Apr. 29, 2015, "SubName: Full= Uncharacterized protein {ECO:0000313IEMBL: KJA27061.1 };", XP002803584, retrieved from EBI accession No. UNIPROT:A0A0D2PEQ0, Database accession No. A0A0D2PEQ0.
Gurung: "Abstract 1000: PD-L 1 binding peptide identified by phage peptide display inhibits PD-1 /PD-L 1 interaction and activates T cells I Cancer Research", Apr. 1, 2018 (Apr. 1, 2018), XP055822659, Retrieved from the Internet: URL: https://cancerres. aacrjournals.org/content/ 78/13_Supplement/1000 [retrieved on Jul. 8, 2021].
Gu Rung Smriti et al: "Phage display-identified PD-L 1-binding peptides reinvigorate T-cell activity and inhibit tumor progression", Biomaterials, Elsevier, Amsterdam, NL, vol. 247, Mar. 20, 2020 (Mar. 20, 2020), XP086130673, ISSN: 0142-9612, DOI: 10.1016/ J.BIOMATERIALS. 2020.119984 [retrieved on Mar. 20, 2020].

* cited by examiner

*Primary Examiner* — Amber D Steele
(74) *Attorney, Agent, or Firm* — Revolution IP, PLLC

(57) ABSTRACT

The present invention relates to a peptide bound to PD-L1 and uses for cancer immunotherapy and anticancer using the same, and the peptide of the present invention specifically binds to PD-L1 and inhibits it, thereby activating the function of immune cells against cancer cells and exhibiting anticancer effects. The peptides of the present invention selected two peptides (PD-L1Pep-1 and PD-L1Pep-2) that bind well to cells with high expression of human PD-L1 protein using phage peptide display technology and it was confirmed that it inhibits its function by binding to PD-L1 in humans and mice. The peptide of the present invention showed an effect similar level to that of an antibody and is relatively stable in blood, indicating a high potential as a cancer immunotherapy in the future.

8 Claims, 7 Drawing Sheets

Specification includes a Sequence Listing.

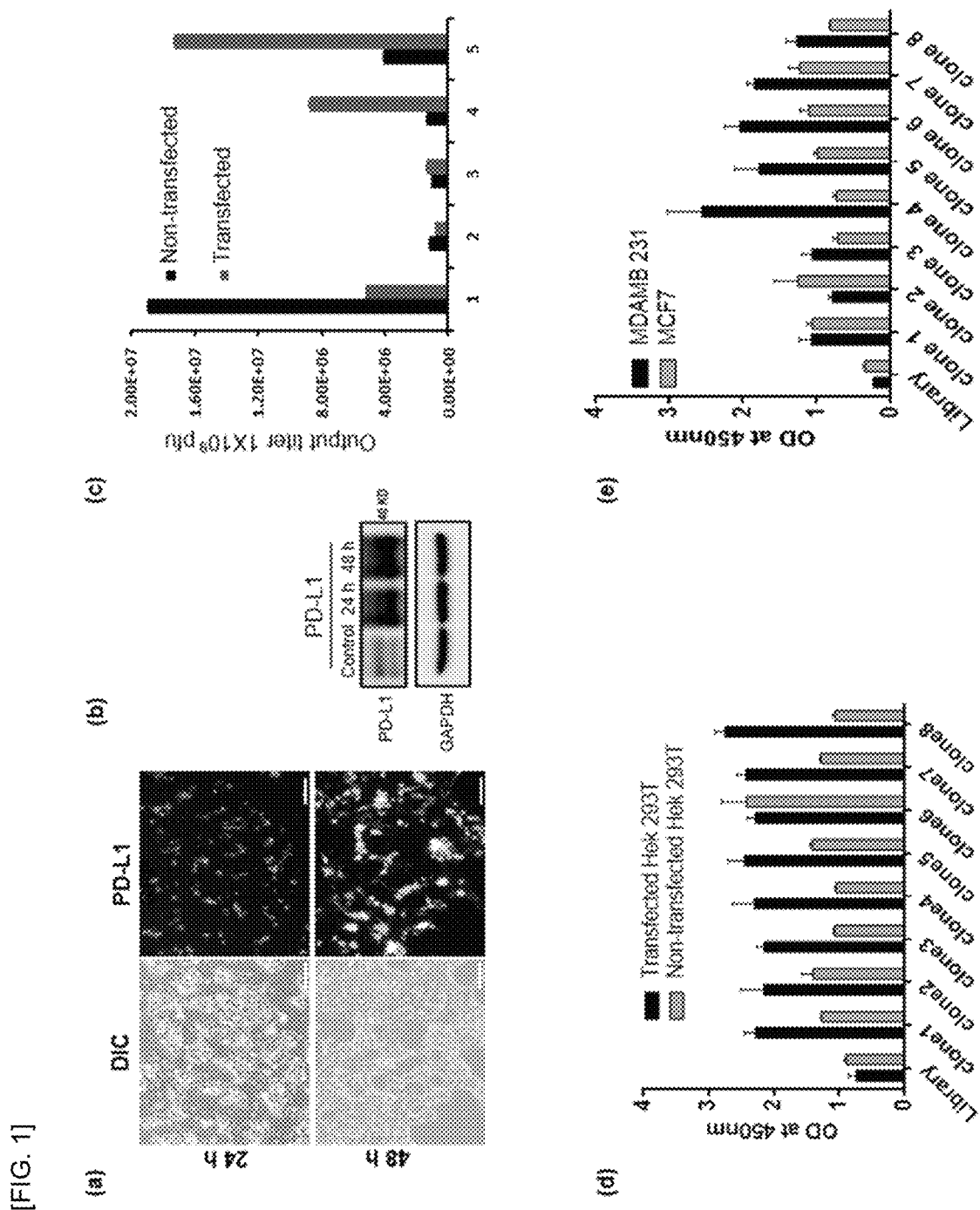
[FIG. 1]

[FIG. 2]
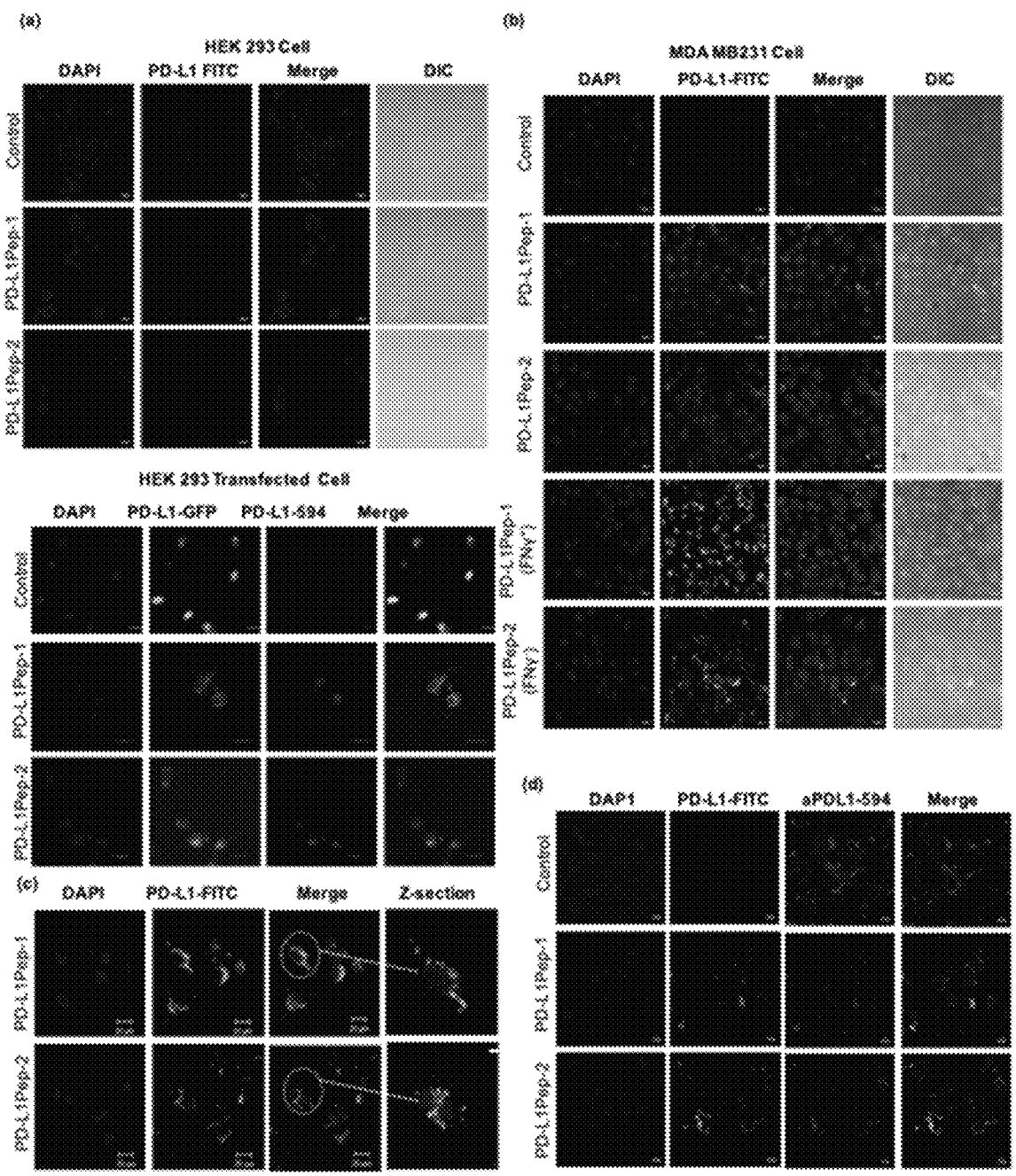

[FIG. 3]
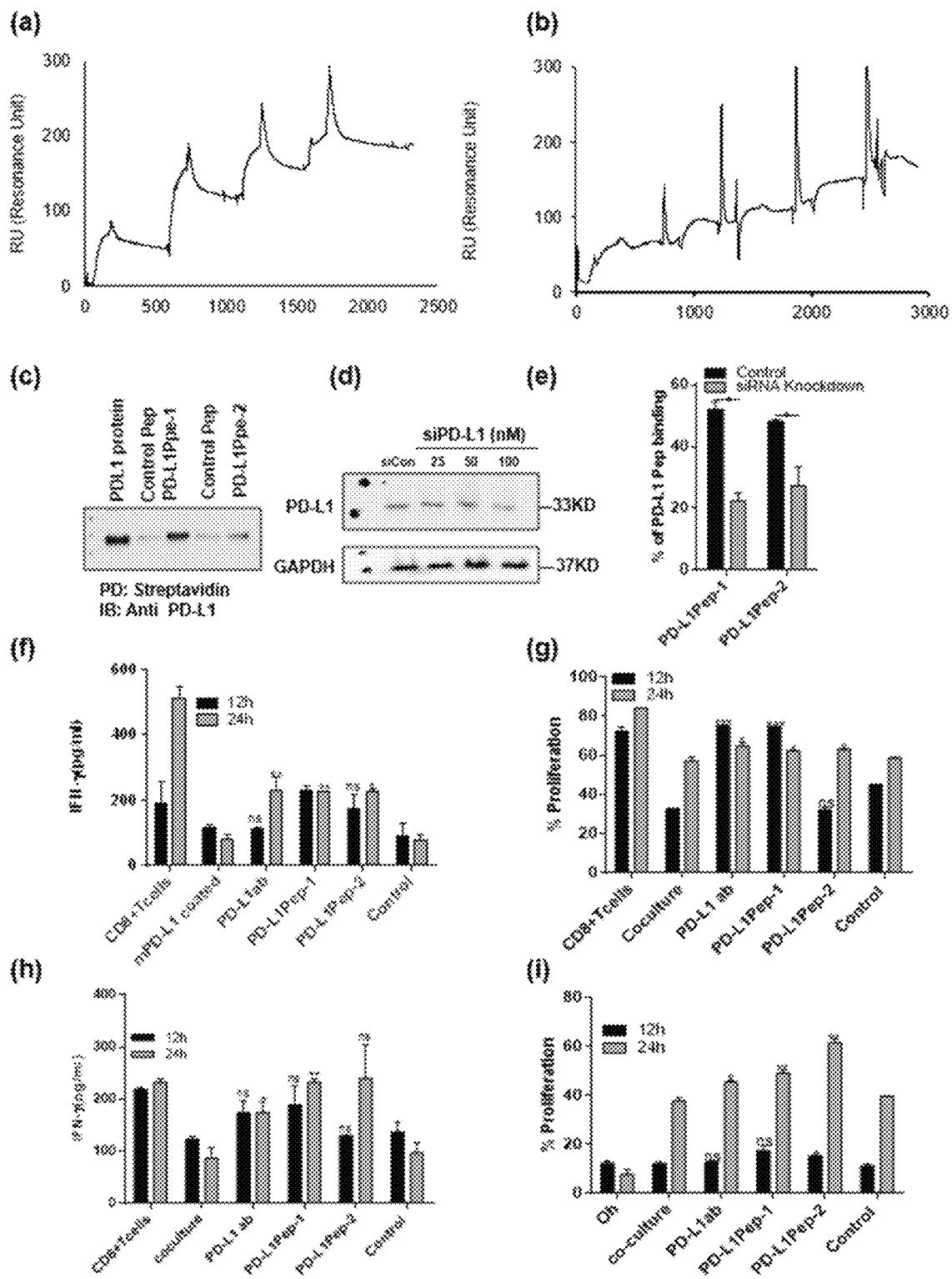

[FIG. 4]
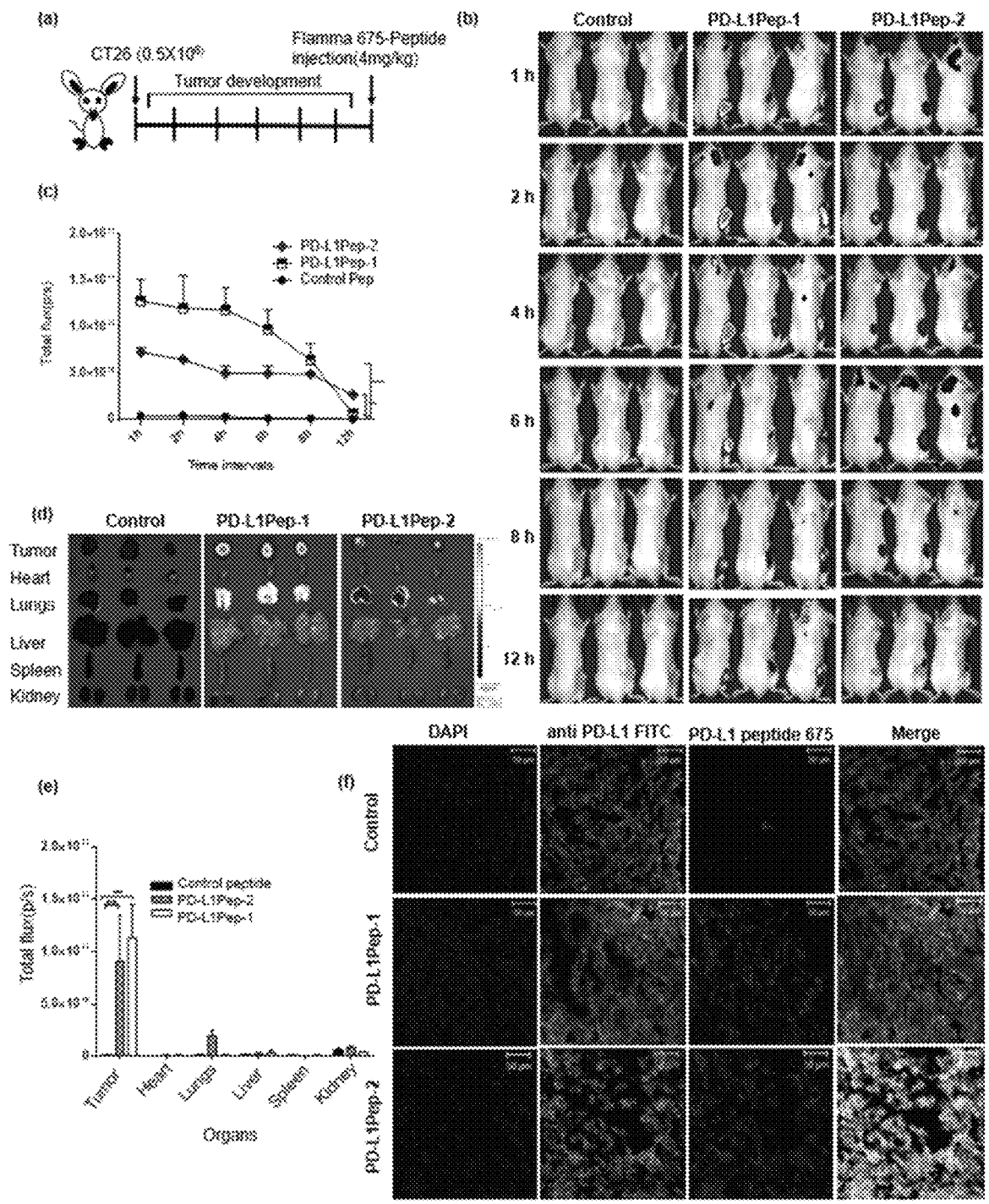

[FIG. 5]
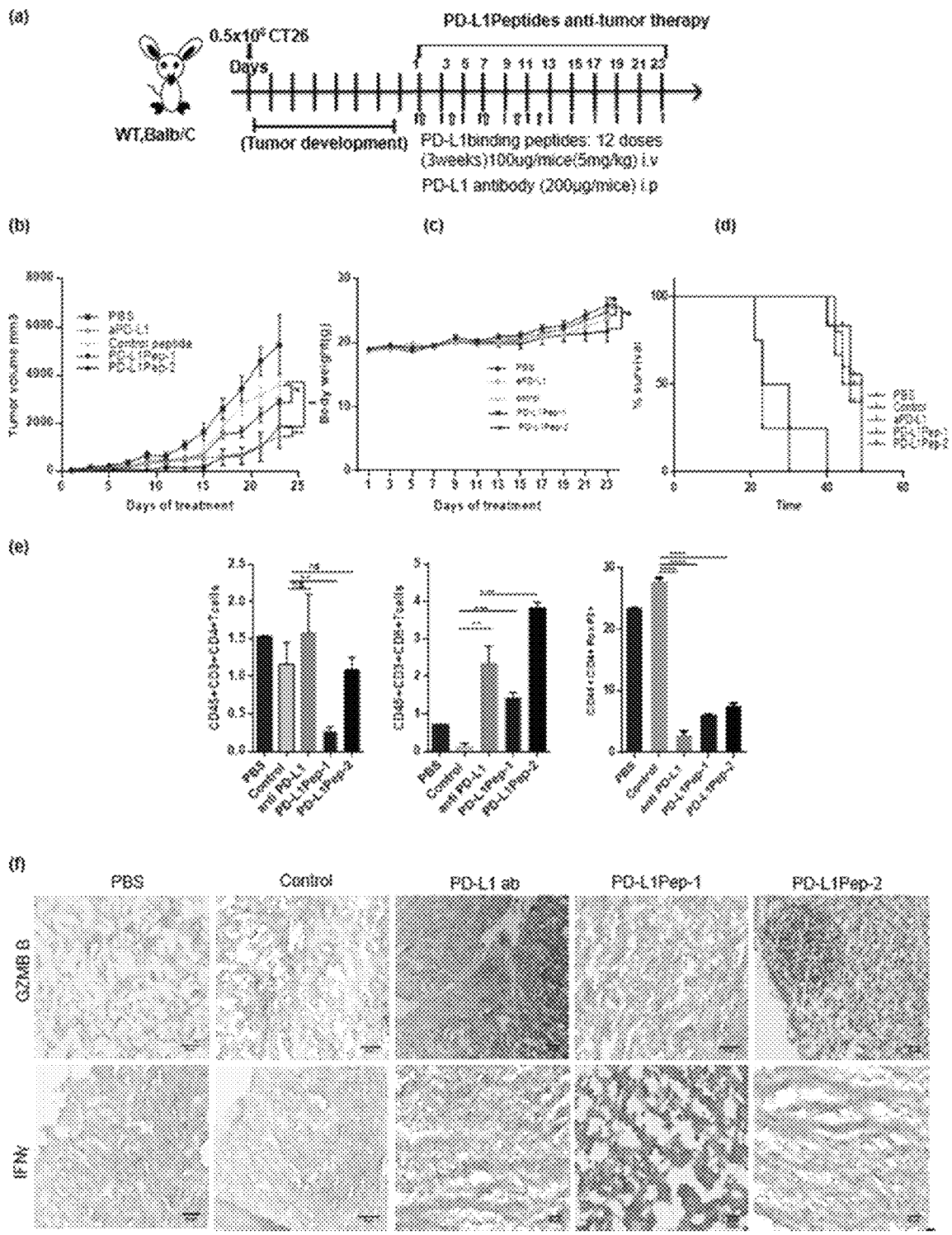

[FIG. 6]
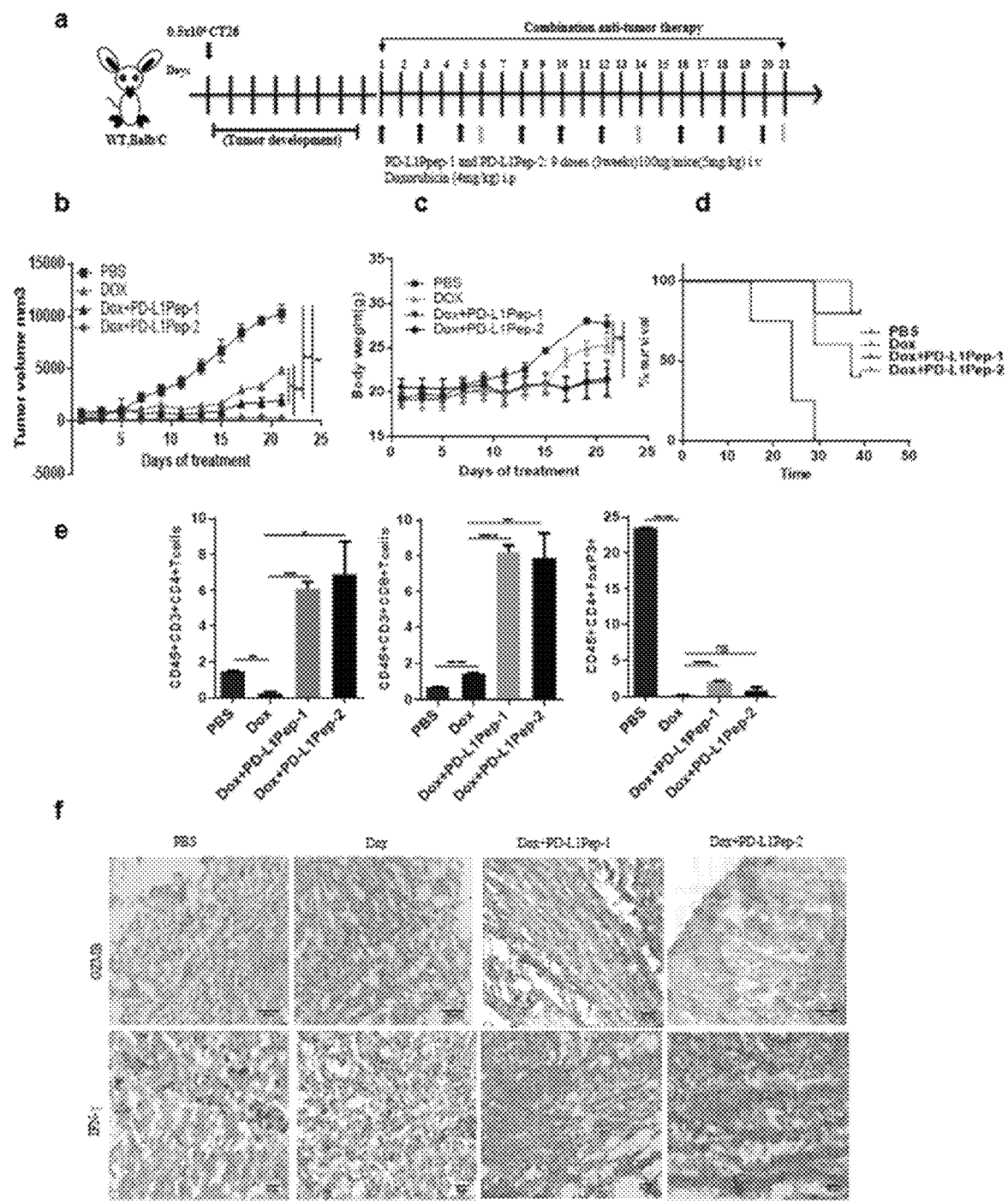

[FIG. 7]
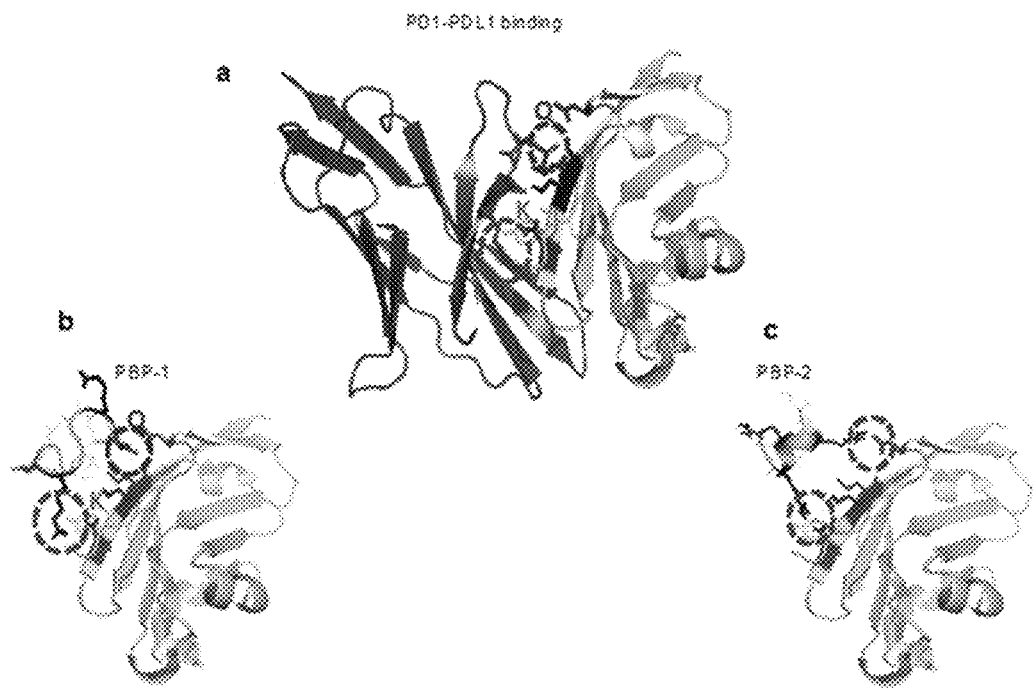
PD-1 extracellular domain
₂₁PGWFLDSPDR ₃₀PWNPPTFSPA ₄₀LLVVTEGDNA ₅₀TFTCSFSNTS ₆₀ESFVLNWYRM ₇₀SPSNQTDKLA ₈₀AFPEDRSQPG ₉₀QDCRFRVTQL ₁₀₀PNGRDFHMSV ₁₁₀VRARRNDSGT ₁₂₀YLCGAISLAP ₁₃₀KAQIKESLRA ₁₄₀ELRVTERRAE ₁₅₀VPTAHPSPSP ₁₆₀RPAGQFQTLV ₁₇₀ (SEQ ID NO: 4)
PBP-1(PD-L1 binding peptide-1)  PBP-2(PD-L1 binding peptide-1)
(CLQKTPKQC) (SEQ ID NO: 1)      (CVRARTR) (SEQ ID NO: 2)

SEQUENCE LISTING

```
<160> NUMBER OF SEQ ID NOS: 4

<210> SEQ ID NO 1
<211> LENGTH: 9
<212> TYPE: PRT
<213> ORGANISM: Artificial Sequence
<220> FEATURE:
<223> OTHER INFORMATION: synthetic peptide

<400> SEQUENCE: 1

Cys Leu Gln Lys Thr Pro Lys Gln Cys
1               5

<210> SEQ ID NO 2
<211> LENGTH: 7
<212> TYPE: PRT
<213> ORGANISM: Artificial Sequence
<220> FEATURE:
<223> OTHER INFORMATION: synthetic peptide

<400> SEQUENCE: 2

Cys Val Arg Ala Arg Thr Arg
1               5

<210> SEQ ID NO 3
<211> LENGTH: 7
<212> TYPE: PRT
<213> ORGANISM: Artificial Sequence
<220> FEATURE:
<223> OTHER INFORMATION: phage coat protein used as control peptide

<400> SEQUENCE: 3

Asn Ser Ser Ser Val Asp Lys
1               5

<210> SEQ ID NO 4
<211> LENGTH: 150
<212> TYPE: PRT
<213> ORGANISM: Human

<400> SEQUENCE: 4

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95
```

-continued

```
Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150
```

PEPTIDE BOUND TO PD-L1 AND USE THEREOF

CROSS REFERENCE TO PRIOR APPLICATIONS

This application is a National Stage Application of PCT International Patent Application No. PCT/KR2018/016021 filed on Dec. 17, 2018, under 35 U.S.C. § 371, which claims priority to Korean Patent Application Nos. 10-2017-0173304 and 10-2018-0161980 filed on Dec. 15, 2017 and Dec. 14, 2018, respectively, which are all hereby incorporated by reference in their entirety.

SEQUENCE LISTING

This application contains a Sequence Listing submitted via EFS-Web and hereby incorporated by reference in its entirety. The Sequence Listing is named SEQCRF-2280-305_rev.txt, created on Jul. 22, 2021, and 2,339 bytes in size.

TECHNICAL FIELD

The present invention relates to a peptide bound to PD-L1 and uses for cancer immunotherapy and anti-cancer using the same.

BACKGROUND ART

The development of cancer immunotherapy has reached an important inflection point in the history of cancer therapy. The programmed cell death (PD-1) pathway has become an attractive therapeutic target in multiple cancers. PD-1 is upregulated on T cells upon activation and remains highly on exhausted T cells, commonly expressed on Tumor-Infiltrating Lymphocytes. Blocking the interaction of PD-1 with its ligand PD-L1 leads to impressive antitumor responses and clinical benefits in a subset of patients.

Recently selective monoclonal antibodies targeting immune checkpoint molecules have received unprecedented success in clinic for the treatment of a board range of the most prevalent human cancer. Survey of large panels of human and mouse tumor samples has revealed that PD-L1 is highly expressed on tumor cells as well as host immune and stromal cells in the tumor microenvironment. PD-L1 is expressed on various types of tumor cells. Blockade of the PD-1/PD-L1 interaction can strengthen the function of effector T cells, reactivated and increases the cytokine production.

Antibodies blocking the PD-1/PD-L1 pathway have demonstrated long-term durable and even complete clinical responses for a significant fraction of patients with a wide variety of advanced and highly refractory cancers. Thus, there are a vast medical need for the development of highly effective and cost-saving therapeutic antibodies against PD-1 and PD-L1. Although a significant number of cancer patient's benefits from PD-1 blockade therapy, many patients fail to have clinical responses. How PD-1 blockade modulates the immune system in cancer patient is only partially understood, and there is an urgent need to uncover factors that determine clinical responses to this therapy also their application is still limited due to high production costs and immunogenicity.

DISCLOSURE

Technical Problem

The present invention relates to a peptide bound to PD-L1 and uses thereof and provides a peptide specifically bound to PD-L1 comprising the amino acid sequence represented by SEQ ID NO: 1 or SEQ ID NO: 2 and a composition for diagnosing cancer, a pharmaceutical composition for preventing or treating cancer, a health functional food composition for preventing or improving cancer and a composition for drug delivery, comprising the peptide as an active ingredient.

Technical Solution

To order to solve the above problems, the present invention provides a peptide specifically bound to PD-L1, comprising the amino acid sequence represented by SEQ ID NO: 1 or SEQ ID NO: 2.

Also, the present invention provides a polynucleotide encoding the peptide, a recombinant vector comprising the polynucleotide and a transformant transformed with the recombinant vector.

In addition, the present invention provides a composition for diagnosing cancer comprising the peptide as an active ingredient.

Furthermore, the present invention provides a pharmaceutical composition for preventing or treating cancer comprising the peptide as an active ingredient.

In addition, the present invention provides a health functional food composition for preventing or improving cancer comprising the peptide as an active ingredient.

In addition, the present invention provides a composition for drug delivery comprising the peptide as an active ingredient.

Advantageous Effects

The present invention relates to a peptide bound to PD-L1 and uses for cancer immunotherapy and anticancer using the same, and the peptide of the present invention specifically binds to PD-L1 and inhibits it, thereby activating the function of immune cells against cancer cells and exhibiting anticancer effects. The peptides of the present invention selected two peptides (PD-L1Pep-1 and PD-L1Pep-2) that bind well to cells with high expression of human PD-L1 protein using phage peptide display technology and it was confirmed that it inhibits its function by binding to PD-L1 in humans and mice. The peptide of the present invention showed an effect similar level to that of an antibody and is relatively stable in blood, indicating a high potential as a cancer immunotherapy in the future.

DESCRIPTION OF DRAWINGS

FIG. 1 shows transient transfection of PD-L1 plasmid vector and bio-panning. (a) The plasmid DNA was transiently transfected and the GFP fluorescence was visualized under microscope for 24 hr and 48 hr (Scale Bar: 20 μm). (b) Immunoblot analysis was performed to confirm the PD-L1 expression in two-time intervals 24 and 48 hr. (c) Five rounds of bio-panning were performed and the phage titer (pfu) was measured after each round. (d) The validation of phage clones was confirmed by phage-binding Elisa in Hek-293 transfected and non-transfected cells (e) also validated in MDAMB 231 and MCF-7 cells. Optical Density (OD) was measured at a wavelength of 450 nm.

FIG. 2 shows cell binding of PD-L1 binding peptides and internalization. (a) HEK-293T cells were transfected with PD-L1 plasmid vector and the binding of the peptides were validated (non-transfected and transfected cells). (b) The binding of PD-L1 binding peptides (PD-L1Pep-1, PD-L1Pep-2) was also confirmed in MDA MB231 cell. (c) Confocal images showed internalization of the PD-L1 peptides. (d) The PD-L1 antibody binding was decreased on the surface of the cells after the internalization of PD-L1 binding peptides (Scale bar: 20 μm).

FIG. 3 shows binding affinity of PD-L1 binding peptide and functional assay. (a, b) The binding affinity of PD-L1Pep-1 and PD-L1Pep-2 was examined by SPR method. (c) PD-L1 recombinant protein was pulled down with streptavidin and immunoblotted with the anti-PD-L1 antibody after reacting the PD-L1 recombinant protein with biotin-peptide. (d) siRNA knockdown of PD-L1 in MDA MB231 cells were confirmed by immunoblotting blotting. (e) Binding percentage of PBPs after the siRNA silencing of PD-L1. (f) Enhanced IFNγ secretion by direct co-culture of mPD-L1 coated plate with CD8+ T cells. (g) T cell proliferation in direct mPD-L1 coated plate (N=3). (h, i) The dendritic cells and the CD8+ T cells were isolated from the OT-I mice co-cultured together in the presence of PD-L1Pep-1 and PD-L1Pep-2 or anti PD-L1 antibody as a positive control. n=3; Mean±SD, *P<0.05, ***P<0.0005 one-way ANOVA.

FIG. 4 shows homing of PD-L1 binding peptide in syngeneic CT26 tumor xenograft mouse model. (a) a schematic diagram for the homing analysis of PD-L1Pep-1 and PD-L1Pep-2 in CT26 tumor cells. (b) Flamma-675 PD-L1Pep-1 and PD-L1Pep-2 were intravenously (i.v) injected into CT26 tumor bearing mice and the images were captured. (c) Quantification of total photon flux (number of photons/second, p/s) at tumor region were calculated. (d) The bio distribution of the PD-L1Pep-1 and PD-L1Pep-2 uptake was seen in all the organs from the mice body. (e) Quantification of total photon flux in total organs. (f) Co-localization of PD-L1Pep-1 and PD-L1Pep-2 was seen in the frozen tumor tissue sections stained with PD-L1 antibody (Scale bar: 50 μm). (n=3; Mean±SD, *P<0.05, ***P<0.0005 one-way ANOVA.

FIG. 5 shows that PBPs inhibited the tumor growth in a syngeneic CT26 tumor xerograph mouse model. (a) a schematic diagram for analyzing the anti-tumor effect of PD-L1Pep-1 and PD-L1Pep-2 in CT26 tumor cells. (b) Tumor volume changes was measured every alternative day for 24 days. (c) The body weight was measured every alternative day during the course of treatment (d) The survival % was also monitored of each group. (n=5; Mean±SD, *P<0.05, ***P<0.0005 Student t-test/one-way ANOVA). (e) Tumor cell analysis on the last day of the treatment was analyzed for CD4+ T cells, CD8+ T cells and Treg cells. (f) IFNγ and granzyme B immunostaining on tumor tissues for each group was evaluated (Scale bar: 50 μm). (n=5; Mean±SD, *P<0.05, ***P<0.0005 one-way ANOVA.

FIG. 6 shows that combinatorial tumor therapy of PD-L1 binding peptide with doxorubicin increased the T cells. (a) A schematic diagram for analyzing the effect of tumor treatment by combinatorial tumor therapy of PD-L1Pep-1 and PD-L1Pep-2 binding peptide with doxorubicin. (b) Tumor volume changes were measured every alternative day. (c) The body weight was measured every alternative day during the course of combination therapy of PD-L1Pep-1 and PD-L1Pep-2 with doxorubicin antitumor treatment. (d) The survival % was also monitored of each group. (n=5; Mean±SD, *P<0.05, ***P<0.0005 Student t-test/one-way ANOVA). (e) Tumor cell analysis was performed to analyze the tumor cell populations. (f) IFNγ and granzyme B immunostaining on tumor tissues for each group was evaluated by confocal microscopy (Scale bar: 50 μm). (n=5; Mean±SD, *P<0.05, ***P<0.0005 one-way ANOVA).

FIG. 7 shows molecular docking analysis of PD-L1 binding peptide interaction with PD-L1. (a) PD-L1/PD-1 binding site. (b) Possible binding site of PD-L1Pep-1 with PD-L1. (C) Possible binding side of PD-L1Pep-2 to PD-L1.

BEST MODE

Therefore, the present inventors used a T7 phage random library to identify peptides specifically bind to PD-L1 and functionally block PD1/PD-L1 interaction and have high affinity. The present inventors have confirmed that PD-L1 blocking on CT26 tumor cells and dendritic cells (DCs) enhances CD8+ T cell proliferation and cytokine production. It was confirmed that the anti-tumor treatment using PD-L1Pep-1 and PD-L1Pep-2 of the present invention has a strong effect on tumor volume and immune cell population in-vivo. As a result, the present inventors have successfully screened peptides that can be effectively used to inhibit PD1/PD-L1 interaction, and confirmed the potential of the peptides as an anticancer drug and completed the present invention.

The present invention provides a peptide specifically bound to PD-L1 comprising the amino acid sequence represented by SEQ ID NO: 1 or SEQ ID NO: 2. In detail, the peptide may block the interaction of PD-1 and PD-L1.

The peptides of the invention can be readily prepared by chemical synthesis known in the art (Creighton, Proteins; Structures and Molecular Principles, W. H. Freeman and Co., NY, 1983). Typical methods include liquid or solid phase synthesis, fragment condensation, F-MOC or T-BOC chemistry method (Chemical Approaches to the Synthesis of Peptides and Proteins, Williams et al., Eds., CRC Press, Boca Raton Fla., 1997; A Practical Approach, Athert on & Sheppard, Eds., IRL Press, Oxford, England, 1989), but they are not limited thereto.

In addition, the peptides of the present invention may be prepared by genetic engineering methods. First, a DNA sequence encoding the peptide is synthesized according to a conventional method. DNA sequences can be synthesized by PCR amplification using appropriate primers. Alternatively, DNA sequences may be synthesized by standard methods known in the art, for example, using an automatic DNA synthesizer (e.g., sold by Biosearch or AppliedBiosystems). The fabricated DNA sequence is inserted into a vector comprising one or more expression control sequences (e.g., promoters, enhancers, etc.) that are operatively linked to the DNA sequence and regulate the expression of the DNA sequence, and transformed the host cell with the recombinant expression vector formed therefrom. The resulting transformant is cultured under appropriate medium and conditions to express the DNA sequence, thereby recovering a substantially pure peptide encoded by the DNA sequence from the culture. The recovery can be performed using methods known in the art (e.g., chromatography). In the above, the term "substantially pure peptide" means that the peptide according to the present invention does not substantially contain any other protein derived from the host.

In the present invention, the peptide represented by the amino acid sequence of SEQ ID NO: 1 or SEQ ID NO: 2 has a concept including functional variants thereof. "Functional variant" refers to all similar sequences in which substitution of some amino acids occurs at amino acid positions that do not affect the properties of the peptides of the invention that specifically bind PD-L1.

In addition, the present invention provides a polynucleotide encoding the peptide.

The "polynucleotide" is a polymer of deoxyribonucleotides or ribonucleotides present in single-stranded or double-stranded form. It encompasses RNA genomic sequences, DNA (gDNA and cDNA) and RNA sequences transcribed therefrom, and includes analogs of natural polynucleotides unless otherwise specified.

The polynucleotide includes not only the nucleotide sequence encoding the peptide, but also a sequence complementary to the sequence. The complementary sequence includes not only perfectly complementary sequences, but also substantially complementary sequences.

In addition, the polynucleotide may be modified. Such modifications include addition, deletion or non-conservative substitutions or conservative substitutions of nucleotides. It is interpreted that the polynucleotide encoding the amino acid sequence also includes a nucleotide sequence showing substantial identity to the nucleotide sequence. The substantial identity may be a sequence that exhibits at least 80% homology, at least 90% homology or at least 95% homology when aligning the nucleotide sequence with any other sequence to the maximal correspondence and analyzing the aligned sequence using an algorithm commonly used in the art.

In addition, the present invention provides a recombinant vector comprising the polynucleotide.

In addition, the present invention provides a transformant transformed with the recombinant vector.

In the present invention, "vector" refers to a self-replicating DNA molecule used to carry a clone gene (or another piece of clone DNA).

In the present invention, "recombinant vector" refers to a plasmid, viral vector or other mediator known in the art capable of expressing a nucleic acid inserted in a host cell and the polynucleotide encoding the peptide of the present invention may be operably linked into a conventional expression vector known in the art. Generally, the recombinant vector may include a replication origin capable of proliferating in a host cell, at least one expression control sequences (e.g., promoters, enhancers, etc.) that control expression, a selective marker and a polynucleotide encoding the peptide of the invention operably linked to the expression control sequences. The transformant may be transformed with the recombinant vector.

Preferably, the transformant can be obtained by introducing a recombinant vector comprising a polynucleotide encoding the peptide of the present invention into host cells by a method known in the art, for example, but not limited to, transient transfection, microinjection, transduction, cell fusion, calcium phosphate precipitation, liposome-mediated transfection, DEAE dextran-mediated transfection, polybrene-mediated transfection, electroporation, gene guns and other known methods for introducing nucleic acids into cells (Wu et al., J. Bio. Chem., 267: 963-967, 1992; Wu and Wu, J. Bio. Chem., 263: 14621-14624, 1988).

In addition, the present invention provides a composition for diagnosing cancer comprising the peptide as an active ingredient.

Preferably, the cancer may be PD-L1 overexpressed cancer, and more preferably, the PD-L1 overexpressed cancer is at least one selected from the group consisting of lung cancer, brain tumor, breast cancer, liver cancer, skin cancer, esophageal cancer, testicular cancer, kidney cancer, colorectal cancer, rectal cancer, stomach cancer, kidney cancer, bladder cancer, ovarian cancer, bile duct cancer, gallbladder cancer, uterine cancer, cervical cancer, prostate cancer, head and neck cancer, pancreatic cancer and squamous cell carcinoma, but it is not limited thereto.

In the present invention, "diagnosis" means identifying the presence or characteristics of a pathological condition. For the purposes of the present invention, diagnosis is to confirm the presence or characteristics of cancer.

Diagnosis of cancer using the peptides of the present invention can be diagnosed by reacting the peptides of the present invention with blood, urine or corresponding tissues or cells obtained directly by biopsy to detect their binding.

In addition, in order to easily identify whether or not the peptide of the present invention has been bound to cancer tissue, to detect and to quantify, the peptide of the present invention may be provided in a labeled state. That is, it can be provided by linking (e.g., covalent bond or bridging) to a detectable label. The detectable label may be a chromogenic enzyme (e.g. peroxidase, alkaline phosphatase), radioactive isotopes (e.g. $^{124}$I, $^{125}$I, $^{111}$In, $^{99m}$Tc, $^{32}$P, $^{35}$S), chromophore, luminescent or fluorescent materials (e.g. FITC, RITC, rhodamine, cyanine, Texas Red, fluorescein, phycoerythrin, quantum dots)) and so on.

Similarly, the detectable label may be an antibody epitope, substrate, cofactor, inhibitor or affinity ligand. Such a labeling may be performed during the process of synthesizing the peptide of the present invention, or may be performed in addition to an already synthesized peptide. If a fluorescent material is used as a detectable label, cancer can be diagnosed by fluorescence mediated tomography (FMT). For example, the peptide of the present invention labeled with a fluorescent material can be circulated into the blood to and observed by fluorescence tomography. If fluorescence is observed, it is diagnosed as cancer.

In addition, the present invention provides a pharmaceutical composition for preventing or treating cancer comprising the peptide as an active ingredient.

In addition, the present invention provides a pharmaceutical composition for preventing or treating cancer comprising a peptide and an anticancer agent as an active ingredient.

Preferably, the anticancer agent may be doxorubicin, paclitaxel, vincristine, daunorubicin, vinblastine, actinomycin-D, docetaxel, etoposide, teniposide, bisantrene, homoharringtonine, gleevec (STI-571), cisplatin, 5-fluorouracil, adriamycin, methotrexate, busulfan, chlorambucil, cyclophosphamide, melphalan, nitrogen mustard or nitrosourea, but it is not limited thereto.

Preferably, the cancer may be PD-L1 overexpressed cancer, and more preferably, the PD-L1 overexpressed cancer is at least one selected from the group consisting of lung cancer, brain tumor, breast cancer, liver cancer, skin cancer, esophageal cancer, testicular cancer, kidney cancer, colorectal cancer, rectal cancer, stomach cancer, kidney cancer, bladder cancer, ovarian cancer, bile duct cancer, gallbladder cancer, uterine cancer, cervical cancer, prostate cancer, head and neck cancer, pancreatic cancer and squamous cell carcinoma, but it is not limited thereto.

Preferably, the pharmaceutical composition can promote the activation of immune cells against cancer cells.

The pharmaceutical composition of the present invention may be prepared using a pharmaceutically acceptable and physiologically acceptable adjuvant in addition to the active ingredient, and the adjuvants include to excipients, disintegrants, sweeteners, binders, coating agents, expanders, lubricants, slip modifiers or solubilizers such as flavoring agent. The pharmaceutical composition of the present invention may be preferably formulated into a pharmaceutical composition by including at least one pharmaceutically acceptable carriers in addition to the active ingredient for administration. Acceptable pharmaceutical carriers in compositions formulated as liquid solutions, which are sterile and biocompatible, can be used by mixing saline, sterile water, Ringer's solution, buffered saline, albumin injection solution, dextrose solution, maltodextrin solution, glycerol, ethanol and one or more of these components and other conventional additives such as antioxidants, buffers and bacteriostatic agents can be added as necessary. In addition, diluents, dispersants, surfactants, binders and lubricants may be additionally added to formulate into injectable formulations such as aqueous solutions, suspensions, emulsions, pills, capsules, granules or tablets.

Pharmaceutical formulation forms of the pharmaceutical composition of the present invention may be granules, powders, coated tablets, tablets, capsules, suppositories, syrups, juices, suspensions, emulsions, drops or injectable solutions and sustained release formulations of active compounds, etc. The pharmaceutical composition of the present invention can be administered by a conventional manner through intravenous, intraarterial, intraperitoneal, intramuscular, intraarterial, intraperitoneal, intrasternal, transdermal, intranasal, inhalation, topical, rectal, oral, intraocular or intradermal routes. The effective amount of the active ingredient of the pharmaceutical composition of the present invention means an amount required for the prevention or the treatment of the diseases. Accordingly, it can be adjusted according to various factors including the type of disease, the severity of the disease, the type and content of active and other ingredients contained in the composition, the type of formulation and the patient's age, weight, general health status, gender and diet, time of administration, route of administration, secretion rate of the composition, duration of treatment, and drugs used simultaneously, but it is not limited thereto, for example, the composition of the present invention may be administered in a dose of 0.1 ng/kg to 10 g/kg when administered once to several times a day for adults.

In addition, the present invention provides a health functional food composition for preventing or improving cancer comprising the peptide as an active ingredient.

The health functional food composition of the present invention may be provided in the form of powder, granule, tablet, capsule, syrup or beverage and the health functional food composition is used with other foods or food additives in addition to the active ingredient, and can be used as appropriate according to a conventional method. The mixing amount of the active ingredient may be appropriately determined according to its purpose of use, for example, prevention, health or therapeutic treatment.

The effective dose of the active ingredient contained in the health functional food composition may be used in accordance with the effective dose of the pharmaceutical composition, but in the case of long-term intake for health and hygiene purposes or for health control purposes, the effective dose may be less than or equal to the above range, and it is clear that it can be used in an amount above the above range because the active ingredient has no problem in safety.

There are no particular restrictions on the type of the health food, for example, meat, sausage, bread, chocolate, candy, snacks, confectionery, pizza, ramen, other noodles, gums, dairy products including ice cream, various soups, beverages, tea, drinks, alcoholic beverages and vitamin complexes, etc.

In addition, the present invention provides a composition for drug delivery comprising the peptide as an active ingredient.

The peptide according to the present invention can be used as an intelligent drug delivery system that selectively delivers drugs to cancer tissues. If the peptide of the present invention is used in the treatment of cancer in connection with a conventionally known drug, since the drug is selectively delivered to cancer tissue and cancer cells by the peptide of the present invention, it can increase the potency of the drug and at the same time significantly reduce the side effects of the drug on normal tissues.

The drug may be an anticancer agent and the anti-cancer agent that can be linked to the peptide of the present invention can be used without limitation as long as it is used in the treatment of conventional cancer. For example, it includes doxorubicin, paclitaxel, vincristine, daunorubicin, vinblastine, actinomycin-D, docetaxel, etoposide, teniposide, bisantrene, homoharringtonine, to gleevec (STI-571), cisplatin, 5-fluorouracil, adriamycin, methotrexate, busulfan, chlorambucil, cyclophosphamide, melphalan, nitrogen mustard and nitrosourea. The linkage between the anticancer agent and the peptide of the present invention can be performed through methods known in the art, such as covalent bonding, crosslinking and the like. To this end, the peptide of the present invention can be chemically modified in a range that does not lose its activity if necessary.

Hereinafter, the present invention will be described in detail with reference to the following examples. The examples are only for describing the present invention in more detail and it is obvious to those skilled in the art that that the scope of the present invention is not limited by these examples embodiments in accordance with the gist of the present invention.

EXPERIMENTAL EXAMPLE

The following experimental examples are intended to provide an experimental example commonly applied to each example according to the present invention.

1. Cell Line and Reagents

Hek-293T (human embryonic kidney), CT26 (mouse colon cancer), MDA MB231 and MCF-7 (human breast cancer cells), were obtained from the American type culture collection (ATCC, Manassas, Va., USA). Hek-293T and MDA MB231 cells were cultured in DMEM low glucose (Gibco, Carslbad, Calif., USA) whereas, CT26 and MCF-7 cells in RPMI-1640 medium (Gibco, Carslbad, Calif., USA) supplemented with 10% fetal bovine serum (Gibco), 100 U/ml of penicillin and 100 ug/ml of streptomycin in $CO_2$ incubator at 37° C.

Recombinant human PD-L1 and Recombinant mouse PD-L1 (Acro Biosystems), Recombinant human IFN-γ (R&D), anti-human PD-L1 (Santa Cruz Biotechnology), antiCD3 and anti CD28 (Bio Xcell), anti mIFNγ (Proteintech), anti-Granzyme B (St John's Laboratory), mouse IL-2, anti-mouse PD-L1, Anti CD8, anti-CD45, anti-CD3, anti-CD4, anti-FoxP3, anti Gr-1, anti F4/80, anti MHCII, anti CD206 mouse PD-1, human PD-1 was all purchased from Bio legend. The PD-L1 antibody for in-vivo experiment was purchased from Bio X cell. Mouse IFN-γ Elisa kit, m IL2 kit, m TNF-a, hIFNγ kit, hIL-2 kit was all purchased from Bio legend. H CD28 and hCD3 from Miltenyi Biotech. CD4+ T cell and CD8+ T cell isolation kit was purchased from Stem cell. CD274 siRNA was purchased from Ambion. Ovalbumin$_{323-339}$ and Ovalbumin$_{257-264}$ was purchased from Sigma Life science. Lipofectamine 2000 was purchased from Invitrogen and the GFP-PD-L1 plasmid vector was from Origene.

2. Bio-Panning Using T7 Phage Peptide Library

The T7 phage peptide library was used by constructing a library after purchasing phage vector from Novagen. Hek-293T cells were cultured in 35 mm dish and transfected with PD-L1 plasmid, when it is 70-80% confluent. The cells were washed 2 times with phosphate-buffered saline (PBS) for 5 mins each. For negative selection or subtraction procedure, the phage library of $1\times10^9$ plaque-forming unit (pfu) was incubated in Hek-293T cells for 1 hr at 4° C. The non-binding phage on these cells were recovered and incubated with PD-L1 transfected Hek 293T cells for 1 hr at 4° C. Uncoupled phage was then washed with PBS containing 10 mg/ml bovine serum albumin (BSA). The phages bound to the cells were eluted by incubation with BL21 (OD: 1) for 10 min at room temperature. The eluates were used for titration and the remaining eluted phage clones were put in 10 ml of BL21 (OD: 0.5) for 3-4 hr until a clear lysis was obtained, as the T7 Phage undergoes lysis cycle. This process was repeated 4 times in total and after serial dilutions, the eluates were inoculated into LB medium Petri plates and incubated overnight at 37° C. The titer of the phage was determined by counting the number of colonies.

3. Sequence Analysis and Peptide Synthesis

After five round of bio-panning, the clones with inserts were confirmed by polymerase chain reaction (PCR). The DNA insert with forty four individual clones were sequenced (Macrogen, Seoul, South Korea). Sequence similarity was identified and aligned using the Clustal W program. As PD-L1 binding peptides, PD-L1Pep-1 (CLQKTPKQC; SEQ ID NO: 1) and PD-L1Pep-2 (CVRARTR; SEQ ID NO: 2) were synthesized (Peptron Inc. Daejeon, Korea). Fluorescein isothiocyanate (FITC), biotin and Flamma-675 were conjugated to the N-terminal of each peptide. Lyophilized peptides were reconstituted with dimethyl sulfoxide (DMSO) to a concentration of 10 mM and then further diluted with phosphate-buffered saline (PBS) to a concentration of 10 µM. NSSSVDK (SEQ ID NO: 3), a peptide sequence present in the phage coat protein, was used as control peptide.

4. Phage Binding Elisa Assay

MDA MB231 and MCF7 ($5\times10^5$) cells were seeded in 96 well plate and incubated overnight. The plates were blocked with 5 mg/ml of BSA at RT for 1 hr. After washing the wells for 6 times with TBST (0.1% Tween20), 100 µl of phage clones ($1\times10^9$ pfu/well) were added and incubated at 4° C. for 1 hr. After washing, horse-radish peroxidase (HRP) conjugated anti T7 tail fiber antibody (diluted in blocking buffer 1:10,000 ratio) were added and incubated at RT for 1 hr. After washing the plates again for 6 times, TMB substrate was added and incubated at RT for 10-15 mins. The reaction was finally stopped by adding 100 µl of 1 $MH_2SO_4$ (stop solution) and the plates were read at 450 nm in a microplate reader.

5. Immunofluorescence and Flow Cytometry Analysis of PD-L1 Peptide Binding

MDA MB231, CT26, MCF7, Hek29 cells ($1\times10^5$) were seeded in eight well chamber slides for overnight. Next day, the cells were washed twice with PBS and incubated with 1% BSA at RT for 1 hr to reduce the non-specific binding of peptides. The cells were then incubated with different concentration (10 mM, 25 mM and 50 mM) of FITC conjugated peptide for 1 hr at 4° C. After fixation, cells were washed, and counter stained with DAPI, mounted and subjected to confocal microscopy (Zeiss, Oberkochen, Germany). For the peptide internalization assay, the MDA MB231 cells were incubated with 25 mM concentration of FITC-conjugated peptides at 37° C. for 1 hr 30 min, the procedure was then continued as previously described. For the receptor internalization assay, first the internalization of peptide was obtained as described above and then after several washing steps with PBS, the PD-L1 antibody (1:100 dilution) was incubated with the cell for 1 hr 30 min at 37° C. Cells were observed with a confocal microscope with the excitation/emission wavelengths of 488 nm/520 nm. For flow cytometry, cells ($1\times10^6$) were harvested and then suspended in the culture medium containing 1% BSA at RT for 1 hr for blocking and then incubated with FITC-labelled PD-L1 for another 1 hr at 4° C. After several washing, 300 ul of cell suspension with PBS was subjected to flow cytometry (BD, Franklin Lakes, N.J.). For the competition analysis with PD-L1 blocking antibody, the cells were incubated with the antibody (1:100 dilution) and then incubated with different concentrations of PD-L1. The cells were fixed and subjected to flow cytometry. For the PD-L1 antibody staining, the cells were blocked with BSA and fixed with PFA, followed by incubation with (1:100 dilution) antibody, In parallel IFN-γ (25 ng/ml) was treated to the cell for 24 hr, washed with PBS followed by the staining with antibody.

6. Binding Specificity of PD-L1 Binding Peptides and Knockdown of PD-L1.

The binding specificity of PD-L1 binding peptides was evaluated by fluorescence-based Elisa analysis. 96 well plate was coated with 100 µl (1 µg/mL) of human PD-L1 and mouse PD-L1, or BSA in TBST (with 0.05% Tween 20) for 1 hr at room temperature. The plates were washed three times and subjected to fluorimeter reader using 488 nm excitation and 515 nm emission wavelength. For siRNA knockdown, MDA MB231 cells were knockdown using 25-100 nM for 24 hr, 48 hr and 72 hr. After the PD-L1 knockdown, the elute was subjected to western blotting using anti PD-L1.

7. Measurement of Kd Value of PD-L1 Binding Peptides

Surface Plasmon Resonance (SPR, Woo jung bsc) was used to examine the affinity constant ($K_D$), Kinetics ($K_a$ and $K_d$). PD-L1 binding peptides (15 µM) were immobilized onto the surface of the SA chip (13206065) and 1 M ethanolamine (pH 8.5) was flowed at 25 µl/min for 8 min. Excess non-bound protein was then removed by flowing 20 Mm HCL for 30 sec, 50 µl/min. PD-L1 protein was then dissolved into the working buffer and flowed at four different concentrations (0.25 µM, 0.5 µM, 1.0 µM, 2.0 µM). Each concentration was injected and flowed at 50 µl/min for 2 min 30 sec. Each RU was recorded. The calculation was done using the Scribber and clamp software.

8. T-Cell Activation Assay and T Cell Proliferation $CD8^+$ T cells were isolated from the spleen of WT Balb/c mice and activated in a CD3 and CD28 coated plate (1 ug/ml) 4° C. overnight. The activated $CD8^+$ T cells were co-cultured with CT26 tumor in a 96 well plate for different time intervals. The CT26 tumor cells was pre-incubated with 10 ug/ml anti PD-L1 antibody and reacted with PD-L1 binding peptides at 25 µM concentration at 4° C. for 1 hr before co-culturing with the activated CFSE-stained $CD8^+$ T cells. Control peptide was also pre-incubated for the comparison. In the parallel experiment, 100 µl of anti-mouse CD3 and CD28 (1 ug/ml) was added into each well of the 96 well plate and incubated at 4° C. overnight. Followed by adding 100 µl of PD-L1 at the final concentration of 0.1 µg/ml and incubated the plates at 37° C. for 3 h, the plates were washed twice with PBS and anti PD-L1 functional blocking antibody and the PD-L1 binding peptides along with the control peptide was added into the corresponding wells, the plates were then incubated for 1 hr at 37° C. followed by twice washing with PBS. Finally, CFSE-stained CD8+ T cells were added with a centrifugation at 250×g for 3 min, the cells were then incubated at cell incubator. Supernatant were harvested after each time incubated and later assessed for IFNγ secretion by using IFNγ detecting ELISA kit and the T-cell proliferation assay was evaluated through FACS analysis. For the proliferation assay, CD8+ T cells were labelled with 5 mM carboxyfluorescein succinimidyl ester (CFSE, Molecular Probes, Eugene, Oreg.) in serum-free RPMI-1640 medium at 37° C. for 20 min, centrifuged and added 500 ul of fresh RPMI media. The fluorescence intensities of CFSE-labelled cells were analyzed using a flow cytometer. The fluorescence intensity of the daughter cells decrease than that of the parental cells after each cell division due to the dilution of CFSE. The percentage of fluorescent cells, except the parental cells were determined in the total population cells.

9. Serum Stability of PD-L1 Targeting Peptides

Mouse blood was collected and allowed to cloth using a microtube for 15-20 min in RT. Serum was then centrifuged at 12000 rpm at 4° C. The upper portion (serum) was collected for testing the peptide stability. The incubated samples were diluted 100-fold and fractionated by C18 reverse phage high performance liquid chromatography (HPLC) with a linear gradient of acetonitrile (0.1% trifluoroacetate in water for equilibration and 0.1% trifluoroacetate in acetonitrile for elution). The peptide peak was collected and vacuum dried.

10. Dendritic Cell Isolation

Dendritic cells were isolated from the spleen of the OT-I mice, the cells were sorted using the marker CDIIb or cultured in the presence of 20 ng/ml of GM-CSF for 7 days. Simultaneously CD8+ T cells were isolated using mouse CD8+ T cell isolation kit. The cells were collected and grown in the Petri dish for 1 day and then the cells were pulsed with 5 ug/ml $Ova_{257-264}$ peptide for 30 min at 37° C. Thereafter, the dendritic cells were then co-cultured with activated CD8+ T cells for different time intervals pre-incubated with anti PD-L1 antibody and PD-L1 binding peptides.

11. In Vivo Homing and Antitumor Therapy 6-8-week-old WT Balb/c mice were purchased. Mice was cared and maintained under the guidelines of the Institutional Animal Care and Use Committee (IACUC) of Kyungpook National University (2014-0001-8.). Tumor was injected onto the lower right flank of the mice. For the in-vivo homing imaging, the tumor was developed for 7 days, after the tumor size reached to 100 mm³, the mice were injected with 100 μl of 100 mM Flamma-675 NIR fluorescence dye labelled peptides and allow the complete circulation for an hour. After incubation, the mice were anesthetized, and the image was taken using the IVIS imaging system. After completing the imaging, the mice were sacrificed and the tumor along with the other organs were isolated out and subjected to ex-vivo imaging using the IVIS imaging machine. For the antitumor therapy the mice were randomized and grouped after the tumor size was reached to approximately 100 mm³. The peptide was then injected intravenously (5 mg/kg) 100 μg/mice for 3 weeks, 3 injections/week. Doxorubicin was injected intraperitoneal (4 mg/kg) once a week. Tumor size was measured using a digital caliper, and the tumor volume was calculated using the formula (Volume ¼ (L–W–H)/2. (Length: longest dimension, Width: shorter dimension, parallel to the mouse body and Height: perpendicular to the length and width). All mice were checked for the ulceration and at the end of the treatment and the mice were sacrificed for the immune cell analysis.

12. Immunofluorescent Analysis of Tissue

To examine the PD-L1 expression and binding of PD-L1 peptides to tissues, mouse CT26 tumor tissues were prepared into frozen section (10 μm thick). The tissue section was blocked with 1%. BSA at RT for 30 min and stained with PD-L1 antibody at 4° C. for 1 h. All tissue sections were counterstained with DAPI, incubated with Prolong Gold anti fade mounting reagent (Life technologies) and observed under a confocal microscope.

13. Flow Cytometry Analysis of Immune Cell Populations in Tumor

Tumors were isolated, minced and incubated with a digestion buffer containing collagenase D (5 mg/ml) with the RPMI-1640 medium at 37° C. for 40 min. The cell suspension was passed through a cell strainer. The single cell suspension was made ready to use and CD45 antibody was used to stain the tumor infiltrating leukocytes and then analyzed with following antibodies for CD4, CD8 and F4/80. The stained cells were then subjected to flow cytometry (Novocyte).

14. Statistical Analysis

Statistical significance was determined by the unpaired Student t test when two groups were compared and one or two-way ANOVA were used for comparisons between multiple groups. Values are presented as the means±SE of 3 independent samples. P values <0.05 were considered as statistically significant.

EXAMPLE

To identify the peptides that can selectively binds to PD-L1 expressing cells or block PD-L1, a T7 phage library of random peptides was screened against PD-L1-overexpressing cells. To prepare PD-L1-overexpressing cells, the GFP-tagged PD-L1 plasmid DNA was transiently transfected in Hek-293T cells and incubated for different time point (24 and 48 h). The expression of GFP-tagged PD-L1 was higher at 48 h than 24 h after transfection, as examined by microscope (FIG. 1a) and western blotting (FIG. 1b). Cells, 48 h after transfection were used for further study. After five rounds of bio-panning against the PD-L1-overexpressing cells, 4 folds of the enrichment of phage titer was obtained compared to that of the first round (FIG. 1c). Forty-four phage clones were randomly picked. The selected individual clones were subjected to polymerase chain reaction and DNA sequencing to know the sequence of the inserted clones. The sequence which appeared onto the non-transfected cells were subtracted from the transfected ones, eight clones with more than 7 amino acid were selected for further validation. Transfected and non-transfected Hek-293T cells were used to validate the binding efficiency of the picked clones by phage binding ELISA (FIG. 1d). MDA MB231 and MCF-7 (positive and negative cell line respectively) were also subjected to assay (FIG. 1e). Based on the binding activity to PD-L1 expressing cells, clone number 4 and 7 were chosen for synthesis (9mer and 7mer) and future studies, the synthesized peptides were named as PD-L1 binding peptides (PD-L1 binding peptides; PD-L1Pep-1). It was named PD-L1Pep-1 (CLQKTPKQC; SEQ ID NO: 1) and PD-L1Pep-2 (CVRARTR, SEQ ID NO: 2).

To investigate the binding activity of PD-L1 binding peptides, the expression level of PD-L1 was checked in four different cancer cell lines, MDA-MB231, CT26, MCF7 and HEK 293 cells by Immunofluroscence staining. MDA-MB231 and CT26 has basal level expression of PD-L1 compared to MCF-7 and HEK 293 cells. The expression level of PD-L1 in MDA-MB231 and CT26 cells was drastically enhanced after the treatment of IFNγ for 24 h, which is already known to be the potent inducer of PD-L1. The PD-L1 binding peptides showed higher binding to HEK 293T cells after transiently overexpressing PD-L1 (FIG. 2a).

Subsequently, both the peptides showed higher binding to MDA-MB 231 cell, and the binding efficiency was increased in an IFNγ treated cells (FIG. 2b). The peptide binding was also increased after the PD-L1 expression was increased with IFNγ treatment at 4° C. However, MCF-7 cell line showed no binding of peptide. In addition, flow cytometry analysis was performed with various concentration of PD-L1 binding peptides, the results indicated that the binding percentage of PD-L1 binding peptides increases with the increasing concentration and relatively showed higher binding in MDA-MB231 cells in comparison to MCF-7 cell. To evaluate the binding specificity of the PD-L1 binding peptide, the MDA-MB 231 cells expressing PD-L1 were blocked with the anti PD-L1 antibody and then subjected to different concentration of PD-L1 binding peptides. As a result, the binding of the PBPs was reduced after the cells were blocked with anti PD-L1 neutralizing antibody. Further, PD-L1 binding peptides was internalized upon incubation at 37° C. Confocal imaging confirmed that both the PD-L1 binding peptides are well internalized (FIG. 2c). After the peptide internalization was confirmed the cells were then stained with PD-L1 antibody. The surface staining of PD-L1 peptides was drastically decreased which clearly confirms the receptor internalization of PD-L1, whereas in the control peptide treated cells the PD-L1 antibody staining did not decrease. (FIG. 2d).

To measure the $K_D$ values of the peptides SPR assays were performed using a streptavidin chip coated with biotin-peptides (FIG. 3a and FIG. 3b). Four different concentrations of PD-L1 binding peptides were for PD-L1Pep-2. Direct binding of the peptides with PD-L1 was further demonstrated by incubation of biotin-peptides and recombinant PD-L1 followed by pull-down with streptavidin and immunoblot with anti-PD-L1 antibody (FIG. 3c). PD-L1 expression was then knocked down in the MDA-MB231 cell expressing PD-L1. siRNA was tested at different concentration (FIG. 3d). After the knockdown of PD-L1 was confirmed by immune blotting, the binding of the PD-L1 binding peptides was evaluated using flow cytometry assay (FIG. 3e), the binding percentage of the peptides was also reduced as the PD-L1 expression was knocked down in MDA-MB231 cells. To further examine the stability of PD-L1 binding peptides, the peptide was incubated with whole serum obtained from mice up to 24 h. The peptide peak remained intact up to 8 h for PD-L1Pep-1 and 4 h for PD-L1Pep-2 and then slowly decreased down. These results demonstrated that the PD-L1 binding peptides was stable up to 4-8 h in the presence of serum.

In order to confirm the direct effect of the PD-L1 binding peptide on PD-1/PD-L1 interaction, the recombinant PD-L1 (0.1 μg/ml) coated plates were pre-incubated with 25 μM of PD-L1 binding peptides, the activated CD8$^+$ T cells was added to each well. In the presence of the PD-L1 antibody and the peptides, T cells released more IFNγ (FIG. 3f) and proliferated significantly (FIG. 3g). Dendritic cells are the professional antigen presenting cells (APC) known to be the strong activator of primary T cell responses. The co-culture experiment with dendritic cells and CD8$^+$ T cells showed the increased release of IFNγ and IL-2 in the presence of PD-L1 antibody and the proliferation of T cells compared to control (FIG. 3h and FIG. 3i). This supports that the PD-L1 binding peptides may block the PD-1/PD-L1 interaction and further proliferate activated T cells.

To examine tumor homing of the peptides, PD-L1 binding peptides were intravenously administered into the wild type mice bearing CT26 tumors (FIG. 4a) of similar size. The IVIS imaging was captured for different time intervals. The 675-flamma tagged PD-L1 binding peptides were accumulated at tumor site at a very high intensity as compared to the control peptide (FIG. 4b). The total body flux intensity was evaluated with a maximum florescence signal at 2 hr circulation after injections (FIG. 4c). Quantitative analysis of ex-vivo images and the total organ flux calculated of tumors and other organs showed the higher accumulation of peptide signal only on to the tumor and a little in lungs and kidney (FIG. 4d and FIG. 4e). The signal in the kidney is probably due to the urinary excretion of peptides. Histological analysis of tumor tissues also confirms the homing of PD-L1 binding peptides to the tumor site expressing high level of PD-L1 (FIG. 4f) These results indicate that PD-L1 binding peptides can selectively target PD-L1 expressing cells in the tumor microenvironment. The homing of the peptides was also confirmed in 4T1 (breast cancer) tumor bearing mice and also in MDA MB231 tumor bearing mice in nude mice.

The antitumor activity was evaluated in a CT26 syngeneic mouse model, as the PD-L1 activity can be observed efficiently in a functional tumor micro environment. PD-L1 peptides was intravenously administered into tumor bearing mice every alternative day for 3.5 weeks (24 days) (FIG. 5a). PD-L1Pep-2 showed a good antitumor therapy by effectively controlling the tumor volume and also PD-L1Pep-1 showed the robust effect compared to the control peptide and PBS group (FIG. 5b). The peptide groups were compared with the anti PD-L1 antibody as the positive control injected intraperitoneally 5 times, the body weight of animals was similar among experimental groups during the treatment (FIG. 5c). The survival percentage of the treated mice was moderate as compared to the control groups (FIG. 5d). Furthermore, the immune cell analysis by flow cytometer reveals that the PD-L1 peptide treatment increased the frequency percentage of cytotoxicity of infiltrating CD8$^+$ T cells and repressed T-reg cell enrichment (FIG. 5e). The immunohistochemistry staining (FIG. 5f) shows the expression of IFNγ and granzyme B was increased in the treated tumor tissue which therefore proves that PD-L1 binding peptides has effectively inhibited the tumor growth, hence reactivating the T cells via blocking the PD-1/PD-L1 interaction.

To enhance the efficacy of immunotherapy with PD-L1-binding peptides, the present inventors combined the peptides with doxorubicin, a chemotherapeutic agent known to induce immunogenic cell death, in CT26 mouse syngeneic colon tumor model. PD-L1 peptides doses were reduced from 12 injections to 9 injections and doxorubicin was given once a week (FIG. 6a). The combination therapy controlled the tumor volume more drastically compared to the previous single treatment (FIG. 6b). In addition, the combination therapy maintained the body weight unchanged compared to the control group, and increased the survival percentage (FIG. 6c and FIG. 6d). The immune cell analysis by flow cytometry showed that the expression percentage of CD8$^+$ T cells in tumor tissue were dramatically increased from 1.5% to 6.2% in the single PD-L1Pep-1 treatment from 3.9% to 7.9% in the case of PD-L1Pep-2. The CD4$^+$ T cells were also increased from 0.4% to 6% and 1% to 6.5% in PD-L1Pep-1 and PD-L1Pep-2, respectively (FIG. 6e). The Immunohistochemistry staining shows the increase in Granzyme B and IFNγ onto the peptide treated groups (FIG. 6f). Therefore, the combination therapy has shown the dramatically increased in the immune cell population and thus the peptides of the present invention support that it further enhances the therapeutic effect when administered in combination with a conventional anticancer chemotherapeutic agent.

Further the possible binding site for PD-L1 binding peptide with PD-L1 was predicted by general docking (FIG. 7). The PD-L1 is depicted in gold color and the important amino acid residue responsible for PD-L1Pep-1 binding is indicated by blue circles (FIG. 7b) and amino acid residues important for binding to PD-L1Pep-2 are also indicated by blue circles (FIG. 7c).

While the present invention has been particularly described with reference to specific embodiments thereof, it is apparent that this specific description is only a preferred embodiment and that the scope of the present invention is not limited thereby to those skilled in the art. That is, the practical scope of the present invention is defined by the appended claims and their equivalents.

The invention claimed is:

1. A peptide that specifically binds to PD-L1, consisting of the amino acid sequence of SEQ ID NO: 1 or SEQ ID NO: 2.

2. A method for diagnosing cancer, comprising:
obtaining a biological sample from the patient;
contacting the biological sample with the peptide of claim 1; and
determining whether or not the peptide is bound to the biological sample.

3. The method of claim 2, wherein the cancer is PD-L1 overexpressed cancer.

4. The method of claim 3, wherein the PD-L1 overexpressed cancer is at least one selected from the group consisting of lung cancer, brain tumor, breast cancer, liver cancer, skin cancer, esophageal cancer, testicular cancer, kidney cancer, colorectal cancer, rectal cancer, stomach cancer, kidney cancer, bladder cancer, ovarian cancer, bile duct cancer, gallbladder cancer, uterine cancer, cervical cancer, prostate cancer, head and neck cancer, pancreatic cancer and squamous cell carcinoma.

5. A method for preventing or treating cancer, comprising a step of administering to a subject in need thereof a pharmaceutical composition comprising the peptide of claim 1 as an active ingredient.

6. The method of claim 5, wherein the cancer is PD-L1 overexpressed cancer.

7. The method of claim 6, wherein the PD-L1 overexpressed cancer is at least one selected from the group consisting of lung cancer, brain tumor, breast cancer, liver cancer, skin cancer, esophageal cancer, testicular cancer, kidney cancer, colorectal cancer, rectal cancer, stomach cancer, kidney cancer, bladder cancer, ovarian cancer, bile duct cancer, gallbladder cancer, uterine cancer, cervical cancer, prostate cancer, head and neck cancer, pancreatic cancer and squamous cell carcinoma.

8. The method of claim 5, wherein the pharmaceutical composition promotes immune cell activation against cancer cells.

* * * * *